(12) United States Patent
Schleicher et al.

(10) Patent No.: US 10,993,696 B2
(45) Date of Patent: May 4, 2021

(54) MULTIPLE TRANSDUCER INJECTION MEASUREMENT

(71) Applicant: Verily Life Sciences LLC, Mountain View, CA (US)

(72) Inventors: Brett Schleicher, San Francisco, CA (US); Benjamin Krasnow, Redwood City, CA (US); Russell Mirov, Los Altos, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 564 days.

(21) Appl. No.: 15/836,425

(22) Filed: Dec. 8, 2017

(65) Prior Publication Data

US 2019/0175145 A1  Jun. 13, 2019

(51) Int. Cl.
*A61B 8/00* (2006.01)
*A61M 5/28* (2006.01)
(Continued)

(52) U.S. Cl.
CPC ............. *A61B 8/4494* (2013.01); *A61M 5/24* (2013.01); *A61M 5/28* (2013.01);
(Continued)

(58) Field of Classification Search
CPC ...... A61M 5/24; A61M 5/28; A61M 5/31511; A61M 5/31568; A61M 5/3148;
(Continued)

(56) References Cited

U.S. PATENT DOCUMENTS

| 4,358,839 A | 11/1982 | Wittke |
| 5,311,871 A * | 5/1994 | Yock ............... A61B 8/0833 |
| | | 600/461 |

(Continued)

FOREIGN PATENT DOCUMENTS

| WO | 2017/189153 A1 | 11/2017 |
| WO | WO2017/189153 | * 11/2017 |

OTHER PUBLICATIONS

International Search and Written Opinion from the International Searching Authority dated Mar. 7, 2019 for International Application No. PCT/US2018/064130, filed Dec. 5, 2018, 14 pages.

(Continued)

*Primary Examiner* — Theodore J Stigell
(74) *Attorney, Agent, or Firm* — Christensen O'Connor Johnson Kindness PLLC

(57) ABSTRACT

A plunger head for a medication injection device includes a first ultrasonic transducer coupled to emit ultrasonic signals, where the first ultrasonic transducer is oriented within the plunger head to send the ultrasonic signals along a length of a barrel of the medication injection device when the plunger head is disposed in the barrel. A second ultrasonic transducer is disposed within the plunger head and oriented to receive reflections of the ultrasonic signals. A controller is disposed in the plunger head and coupled to the first ultrasonic transducer and the second ultrasonic transducer. The controller includes logic that when executed by the controller causes the controller to perform operations including instructing the first ultrasonic transducer to emit the ultrasonic signals.

15 Claims, 6 Drawing Sheets

(51) Int. Cl.
*A61M 5/315* (2006.01)
*A61M 5/24* (2006.01)
*A61B 5/145* (2006.01)
*A61M 5/31* (2006.01)

(52) U.S. Cl.
CPC .... *A61M 5/31511* (2013.01); *A61M 5/31568* (2013.01); *A61B 5/14532* (2013.01); *A61B 8/543* (2013.01); *A61B 2562/06* (2013.01); *A61M 5/3148* (2013.01); *A61M 2205/3375* (2013.01); *A61M 2205/3379* (2013.01); *A61M 2205/50* (2013.01); *A61M 2205/52* (2013.01); *A61M 2205/8206* (2013.01); *A61M 2205/8243* (2013.01)

(58) Field of Classification Search
CPC ......... A61M 2205/3375; A61B 8/4494; A61B 5/14532; A61B 8/543
See application file for complete search history.

(56) References Cited

U.S. PATENT DOCUMENTS

| | | | |
|---|---|---|---|
| 5,678,189 A | 10/1997 | Barnes | |
| 5,728,074 A | 3/1998 | Castellano et al. | |
| 5,826,066 A | 10/1998 | Jardine et al. | |
| 6,585,698 B1 | 7/2003 | Packman et al. | |
| 7,927,281 B2 | 4/2011 | Wheeler | |
| 8,226,599 B2 | 7/2012 | Engle | |
| 8,556,866 B2 | 10/2013 | Krulevitch et al. | |
| 8,560,271 B2 | 10/2013 | Koehler et al. | |
| 8,817,258 B2 | 8/2014 | Whalley et al. | |
| 9,008,764 B2 | 4/2015 | Larsen | |
| 9,101,723 B2 | 8/2015 | Larsen | |
| 9,250,111 B2 | 2/2016 | Whalley et al. | |
| 9,255,830 B2 | 2/2016 | Whalley et al. | |
| 9,861,756 B1* | 1/2018 | Krasnow | G01F 11/027 |
| 10,413,676 B1* | 9/2019 | Krasnow | A61B 5/0026 |
| 2005/0209601 A1 | 9/2005 | Bowman et al. | |
| 2008/0188813 A1 | 8/2008 | Miller et al. | |
| 2008/0243088 A1 | 10/2008 | Evans | |
| 2009/0043253 A1 | 2/2009 | Podaima | |
| 2009/0069742 A1 | 3/2009 | Larsen | |
| 2011/0009824 A1 | 1/2011 | Yodfat et al. | |
| 2012/0101451 A1 | 4/2012 | Boit et al. | |
| 2012/0302849 A1 | 11/2012 | Grant et al. | |
| 2013/0116666 A1 | 5/2013 | Shih et al. | |
| 2013/0310756 A1 | 11/2013 | Whalley et al. | |
| 2014/0249410 A1 | 9/2014 | Uber et al. | |
| 2014/0379874 A1 | 12/2014 | Starr et al. | |
| 2015/0112316 A1 | 4/2015 | Cudak et al. | |
| 2015/0174342 A1* | 6/2015 | Mitrosky | A61M 5/31525 604/506 |
| 2015/0209510 A1 | 7/2015 | Burkholz et al. | |
| 2015/0217059 A1 | 8/2015 | Ashby et al. | |
| 2015/0273145 A1 | 10/2015 | Nessel et al. | |
| 2016/0030683 A1 | 2/2016 | Taylor et al. | |
| 2016/0074587 A1 | 3/2016 | Searle et al. | |
| 2016/0279324 A1 | 9/2016 | Uber et al. | |
| 2017/0246399 A1 | 8/2017 | Forlani et al. | |
| 2017/0316177 A1* | 11/2017 | Mirov | A61M 5/31511 |
| 2019/0054252 A1* | 2/2019 | Amschler | A61M 5/31571 |
| 2019/0083715 A1* | 3/2019 | Redmond | A61M 5/31568 |

OTHER PUBLICATIONS

International Search Report and Written Opinion dated Jun. 8, 2017, for International Application No. PCT/US2017/017821, filed Feb. 14, 2017, 16 pages.
U.S. Appl. No. 15/133,396, filed Apr. 20, 2016.
U.S. Appl. No. 62/305,067, filed Mar. 8, 2016.

* cited by examiner

MULTIPLE TRANSDUCER INJECTION MEASUREMENT

TECHNICAL FIELD

This disclosure relates generally to drug injection and in particular but not exclusively, relates to tracking injection quantities.

BACKGROUND INFORMATION

Measuring the quantity and recording the timing of a drug's administration is an integral part of many disease treatments. For many treatments, to achieve the best therapeutic effect, specific quantities of a drug may need to be injected at specific times of day. For example, individuals suffering from diabetes may be required to inject themselves regularly throughout the day in response to measurements of their blood glucose. The frequency and volume of insulin injections must be carefully tracked and controlled to keep the patient's blood glucose level within a healthy range.

Currently, there are a limited number of methods or devices capable of tracking drug administration without requiring the user to manually measure and record the volume, date, and time. A variety of glucose injection syringes/pens have been developed, but there is much room for significant advancement in the technology in order to reduce the size, lower the cost, enhance the functionality, and improve the accuracy. Thus, the current technology may not be an ideal long-term solution. For example, current insulin pens are often disposable, but do not include dosage tracking. A smaller portion of the market is composed of reusable pens which are more expensive, and still do not include accurate dosage-tracking capabilities.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Figure 1:
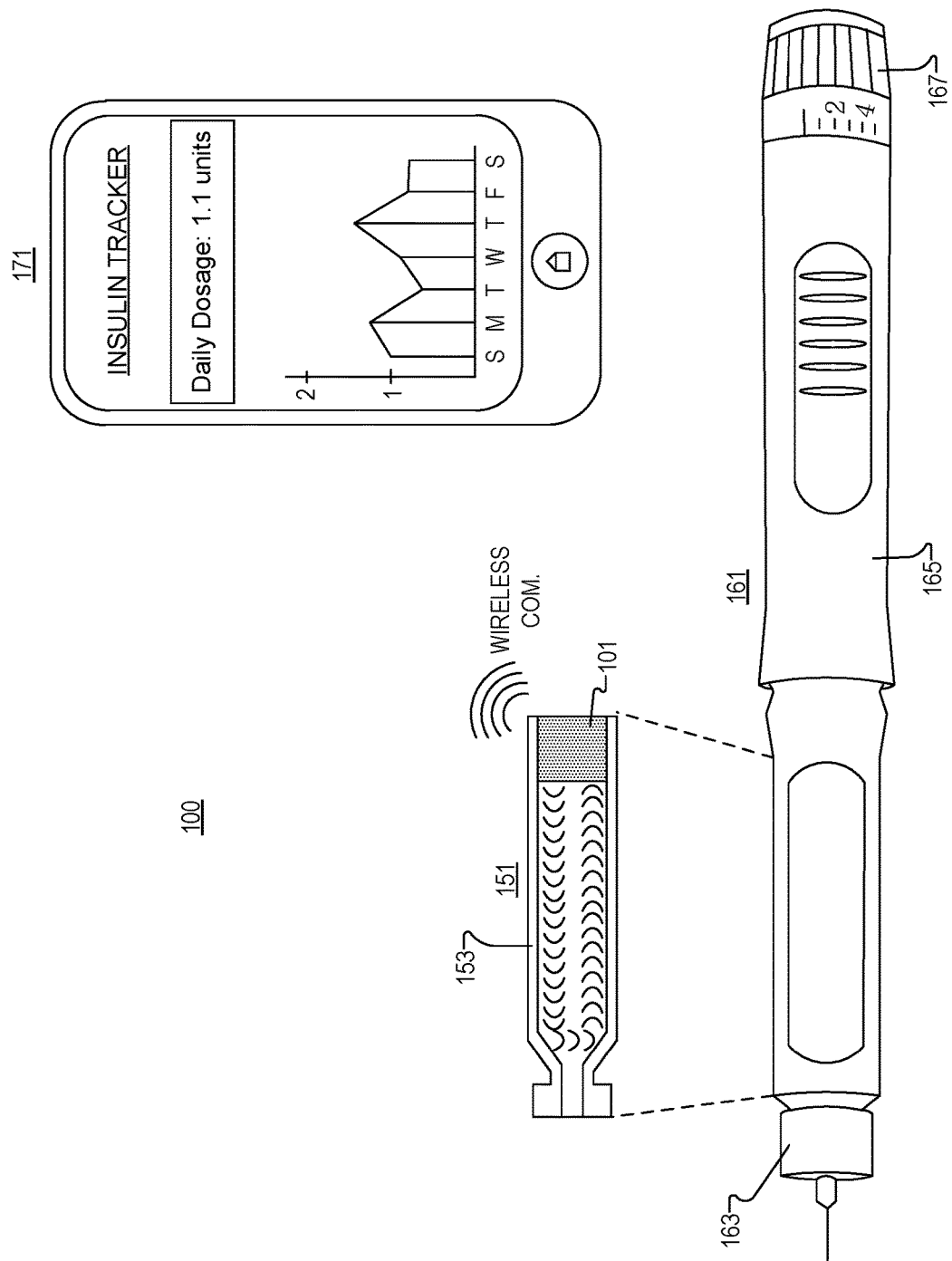
FIG. 1 illustrates an injection pen system, in accordance with an embodiment of the disclosure.

Embodiments of an apparatus and method for multiple transducer injection measurement are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

When using ultrasonic time-of-flight range finding, it is often difficult to measure short distances because the transmit pulse may overlap the echo. The transmit pulse can be shortened by some methods, but the transducer is physically resonating, and this energy cannot be dissipated quickly enough in some instances. In the case of a small, low-cost range finding system, it is desirable for the solution to this problem to be inexpensive and not require sophisticated circuitry or structures that are difficult to manufacture.

In the application of the rangefinder in a drug delivery device, there is an interesting geometrical consideration that makes the positioning of two or more transducers especially relevant. The cartridge (or syringe) that contains the liquid drug has a narrowing shoulder region at the point where the cartridge transitions from its main body diameter to the neck (e.g., narrow region where fluid is dispensed from). This narrowing portion, or shoulder region, of the cartridge functions like an acoustic mirror (e.g., shaped to focus sound waves), reflecting some of the acoustic signal from one side of the cartridge to the other, at a nearly 90° angle from the incoming beam. The reflected beam hits the other side of the cartridge, and is reflected again at 90°, sending the beam back toward the stopper, but along the opposite side of the cartridge. Thus, having separate transmit and receive piezo elements is advantageous when they are spaced the same distance as the shoulder separation at the cartridge tip. Additionally, placing the transducers in the plunger head (instead of other locations in the injection system) conveys significant advantages. For example, the plunger head may be manufactured separately from the rest of the device, using different manufacturing processes/techniques, which may lower costs. Additionally, as shown here, the plunger head may be adapted for multiple types of ultrasonic rangefinding injection systems and can be installed as an aftermarket attachment.

FIG. 1 illustrates an injection pen system 100, in accordance with an embodiment of the disclosure. Pen system 100 includes injection pen 161, drug cartridge 151, and processing device 171 (e.g., a smart phone).

Drug cartridge 151 includes cartridge body 153, and plunger head 101. In the depicted embodiment, plunger head 101 starts near the rear of drug cartridge 151 and is pushed forward in drug cartridge 151 (with a plunger disposed in injection pen 161). This forces medication/fluid from the narrow end of drug cartridge 151 when a user choses to dispense a fluid. In one embodiment, cartridge body 153 incudes borosilicate glass, and plunger head 101 includes an elastomer.

Although depicted in greater detail later, plunger head 101 is a "smart" plunger head that can be used to calculate a quantity of fluid dispensed from drug cartridge 151. Accordingly, plunger head 101 includes a first ultrasonic transducer coupled to emit ultrasonic signals (curved lines traveling away from plunger head 101) along a length of the barrel when the plunger head 101 is disposed in the barrel. A second ultrasonic transducer is disposed within plunger head 101 and oriented to receive reflections of the ultrasonic signals (curved lines traveling towards plunger head 101). The first and second ultrasonic transducers may be made from an actuator, piezoelectric element, or speaker-like voice coils, or the like. A controller is disposed in plunger head 101 and is coupled to the first ultrasonic transducer and the second ultrasonic transducer. The controller includes logic that when executed by the controller causes the controller to perform operations including instructing the first ultrasonic transducer to emit the ultrasonic signals. It is worth noting that the controller may be disposed in anywhere in the plunger head 101 or injection pen 161, in accordance with the teachings of the present disclosure.

In the depicted embodiment, the controller in plunger head 101 may receive an electrical signal from the second ultrasonic transducer, in response to the second ultrasonic transducer receiving the ultrasonic signals. The controller may use this signal to calculate a time of flight for the ultrasonic signals to travel from the first ultrasonic transducer to a dispensing end of the barrel and be reflected back into the second ultrasonic transducer. In other words, the controller may determine the difference in time between the ultrasonic signal being emitted, and the ultrasonic signal being received. This time of flight may then be used to calculate a position of the plunger head. If the time of flight is correlated to the plunger head's position in the barrel, the controller can determine the amount of fluid dispensed based on the time of flight (e.g., $(P1-P2)\pi r^2$, where r is the inner radius of the barrel, and P1 and P2 are the first and second positions of the plunger head in the barrel, respectively). Accordingly, once the time of flight is known, the controller may calculate a wide array of information about the fluid dispensed.

Injection pen 161 is a hand-held device and includes needle 163, body 165 (including the plunger to push in plunger head 101 and extract fluid from drug cartridge 151), and drug delivery control button 167 (twist button 167 to "click" control the dosage, press button 167 to dispense the fluid from drug cartridge 151). As shown, body 165 is configured accept drug cartridge 151. In the depicted embodiment, drug cartridge 151 may be disposed in an insert which screws/snaps onto the bulk of body 165. However, as one of ordinary skill in the art will appreciate, injection pen 161 can take other configurations and have other components. Further, injection pen 161 may be a commercially available injection pen.

Processing device 171 (e.g., a smartphone, tablet, general purpose computer, distributed system, servers connect to the internet, or the like) may be coupled to receive dosage data from plunger head 101 (or injection pen 161—depending on where the transmitter is located) to store/analyze this data. For instance, in the depicted embodiment, processing device 171 is a smartphone, and the smartphone has an application running recording how much insulin has been spent from injection pen 161. Moreover, the application is plotting how much insulin has been injected by the user over the past week.

Figure 2:
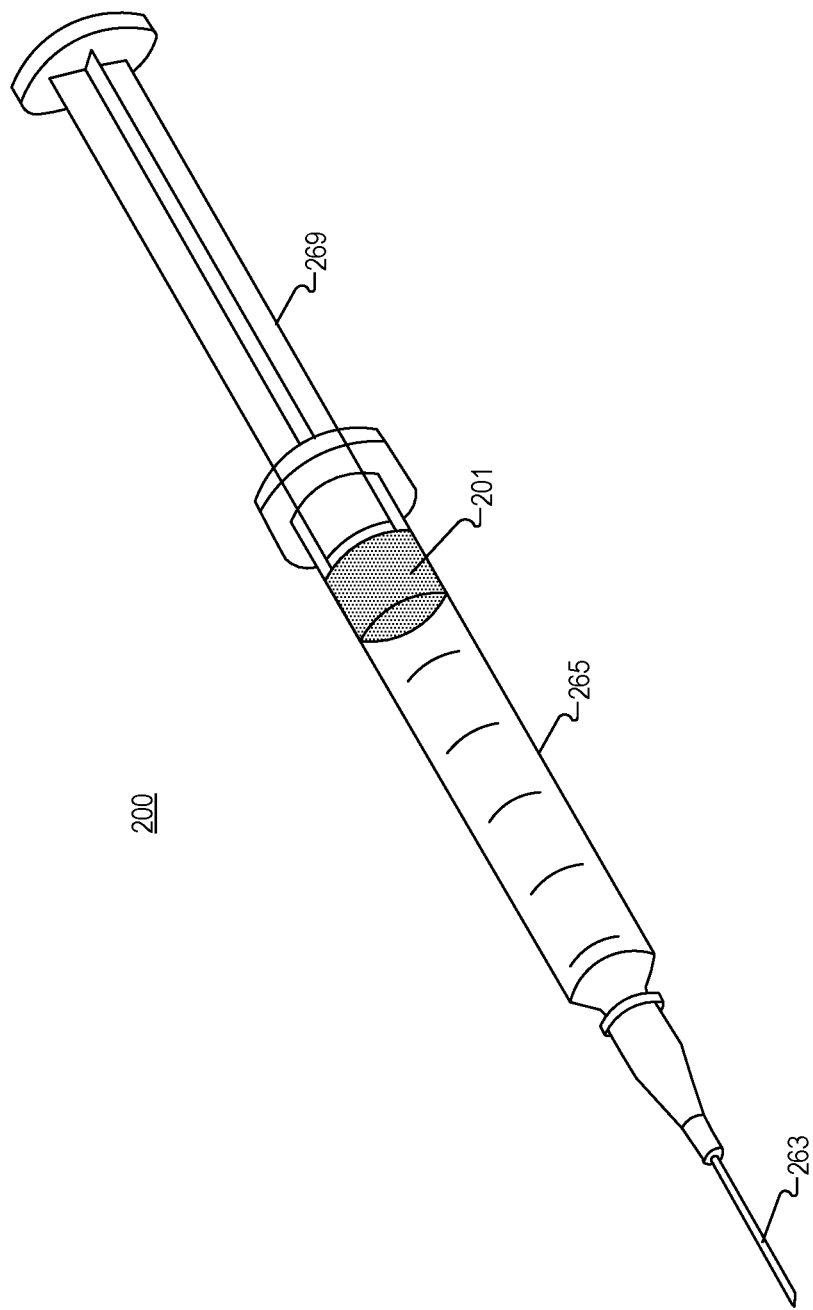
FIG. 2 illustrates a syringe system, in accordance with an embodiment of the disclosure.

FIG. 2 illustrates a syringe 200 system, in accordance with an embodiment of the disclosure. As illustrated, plunger head 201 (which may have all the same components as plunger head 101 in FIG. 1) may have been placed in body 265 of syringe 200 in order to measure dosage quantity, temperature of the medication, conductivity of the medication or the like. Plunger head 201 may be installed in a standard syringe 200 by withdrawing plunger 269, removing the standard plunger head, and installing plunger head 201. In some embodiments, syringe 200 may be manufactured and supplied with a plunger head 201 preinstalled. Plunger head 201 may be sized to correspond with the size of body 265. For example, plunger head 201 may be formed to fit any size syringe 200. Needle 263 may come preinstalled or be attached by the user. Since the shoulder region is shaped similarly to the shoulder region of a drug cartridge (e.g., drug cartridge 151 in FIG. 1, see also drug cartridge 351 in FIG. 3), plunger head 201 can send and receive ultrasonic signals in syringe 200 in almost the same way as it can in a drug cartridge.

Figure 3:
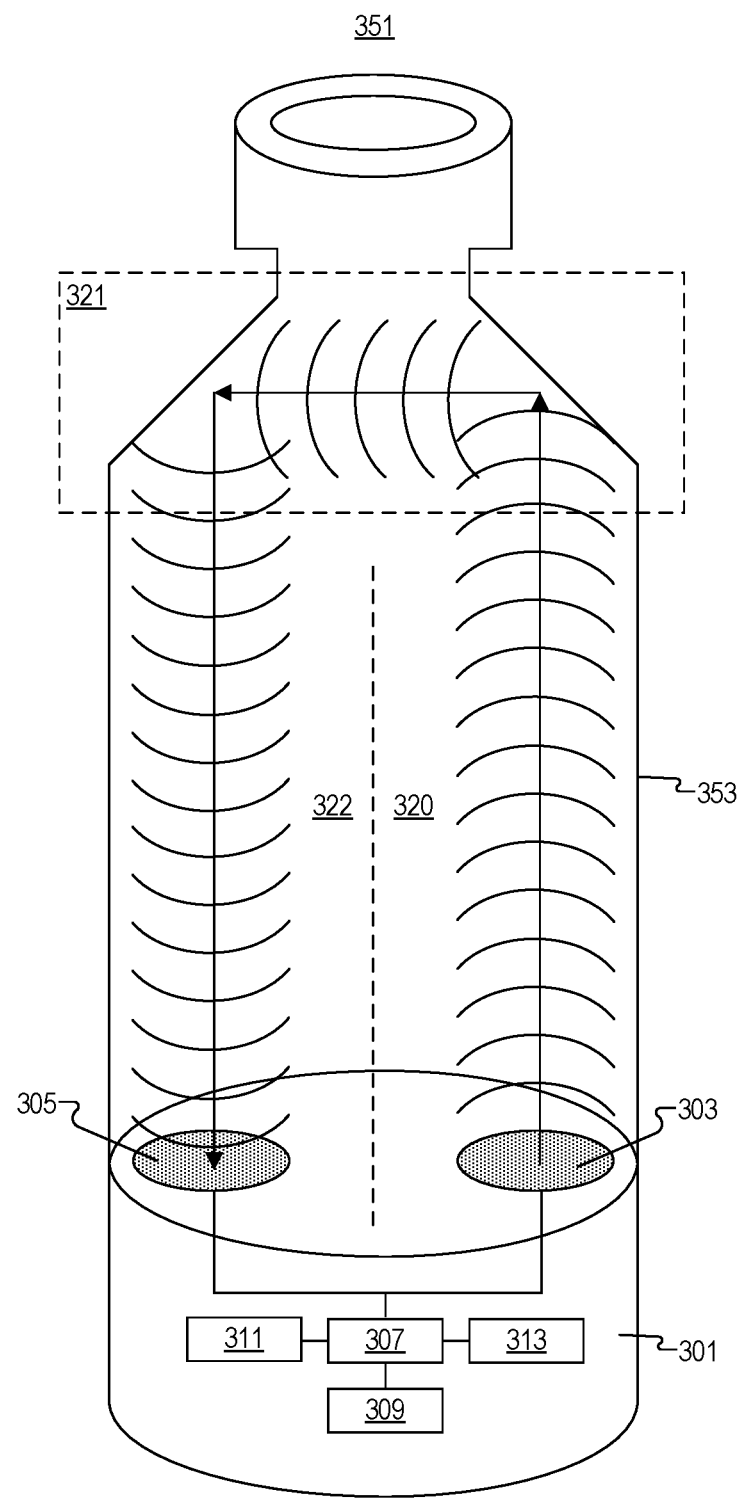
FIG. 3 illustrates an example of multi-transducer ultrasonic range finding, in accordance with an embodiment of the disclosure.

FIG. 3 illustrates an example of multi-transducer ultrasonic range finding, in accordance with an embodiment of the disclosure. The depicted embodiment includes an injection pen cartridge 351 (with shoulder region 321), and plunger head 301. Plunger head 301 includes first ultrasonic transducer 303, second ultrasonic transducer 305, controller 307, power supply 309, memory 311, and transceiver 313 (e.g., Bluetooth, RFID, or the like). One of ordinary skill in the art will appreciate that other pieces of circuitry may be present in plunger head 301 but are not depicted here to avoid obscuring certain aspects of the disclosure. For example, plunger head 301 may also include a temperature sensor to measure the temperature of the fluid in the cartridge 351/syringe, electrodes to measure conductivity of the fluid, a time keeper distinct from controller 307 (e.g., an oscillator), or the like. In the depicted embodiment, controller 307 is coupled to ultrasonic transducers 303/305 to control the emission of the ultrasonic signals and measure when the ultrasonic signals are received.

Controller 307 includes memory 311 and memory 311/controller 307 may include logic that when executed by controller 307 causes controller 307 to perform a series of operations. Memory 311 may include RAM, ROM, or the like. Power supply 309 may include a battery (such as a lithium ion battery or the like), and may be coupled to a charging input such as an inductive charging loop or a direct electrical input (e.g., micro connection or the like). Power supply 309 is coupled to controller 307 and the other pieces of circuitry. Transceiver 313 is coupled to controller 307 to wirelessly communicate with an external device. In some embodiment, transceiver 313 may be a single device to send and receive signals, may be exclusively a transmitter, or may contain a dedicated transmitter and receiver.

As shown cartridge 351, has a narrowing shoulder region 321 at the point where cartridge 351 transitions from its main body 353 diameter to the neck (narrow region where fluid is dispensed from). As shown first ultrasonic transducer 303 and second ultrasonic transducers 305 are disposed proximate to opposite lateral sides (e.g., first side 320 and second side 322, formed by an imaginary plane between the two halves of the device) of the plunger head 301. Thus, shoulder region 321 of cartridge 351 functions like an acoustic mirror, the first side 320 of the shoulder region 321 reflects some of the acoustic signal to the second side of cartridge 351 at a nearly 90° angle from the incoming beam. The reflected beam hits the second side 322 of cartridge 351, and is reflected again at 90°, thus sending the beam back toward second ultrasonic transducer 305, but along the opposite side of cartridge 351. Thus, having separate ultrasonic transducers to send (303) and receive (305) ultrasonic signals may be advantageous when they are spaced the same distance as the shoulder region 321 separation. One of ordinary skill in the art will appreciate that the system depicted is also applicable to a syringe barrel since the shoulder region 321 geometry of a syringe may be similar, and a "smart" plunger headlike the one shown can also be placed in a syringe (see e.g., FIG. 2).

In one embodiment, an emission bandwidth of first ultrasonic transducer 303 is greater than a receiving bandwidth of second ultrasonic transducer 305, but wavelengths in the emission bandwidth are included in the receiving bandwidth. Moreover, lenses may be used to focus the emission of the ultrasonic waves from first ultrasonic transducer 303. Similarly, lenses may be used to focus the received ultrasonic signals into second ultrasonic transducer 305. Lensing may be achieved using any material that changes the speed of the ultrasonic signals (relative to the speed of the ultrasonic signals in the fluid). Further, during the emission of the ultrasonic waves from first ultrasonic transducer 303, controller 307 may disable (e.g., short to ground) the second ultrasonic transducer 305. This prevents emission vibrations from being registered by second ultrasonic transducer 305 as received ultrasonic signals. Moreover, one of ordinary skill in the art will appreciate that a number of signal filtering methods may be used to isolate the receipt of actual ultrasonic signals (not just random vibrations and reflections). For example, high pass, low pass, or bandpass filters may all be used to isolate the actual signal reflected from vibrations and noise.

FIGS. 4A-4F illustrate multi-transducer plunger heads which may be used in the systems depicted in FIGS. 1 and 2, in accordance with several embodiments of the disclosure. One of ordinary skill in the art will appreciate that the six plunger head configurations depicted are not exhaustive; other multi-transducer plunger heads may be fabricated in accordance with the present disclosure. Moreover, the different shapes/configurations depicted may be combined in any suitable manner.

Figure 4B:
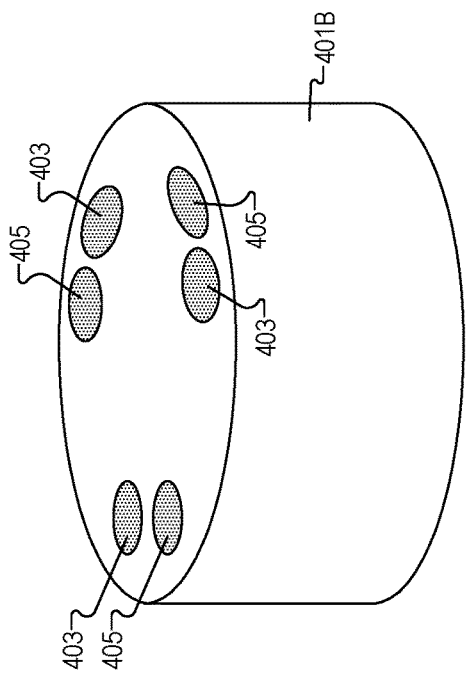
FIGS. 4A-4F illustrate multi-transducer plunger heads which may be used in the systems depicted in FIGS. 1 and 2, in accordance with several embodiments of the disclosure.
Figure 4D:
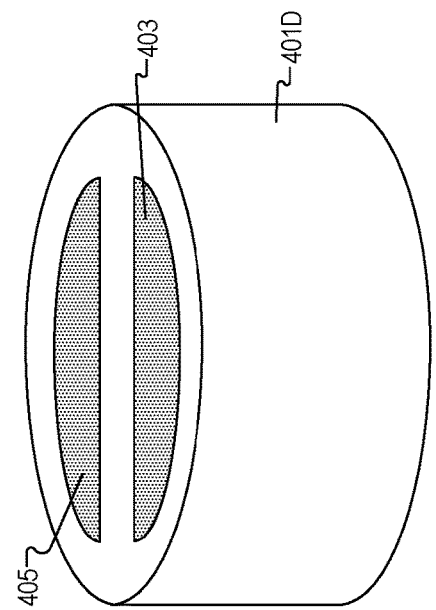
Figure 4A:
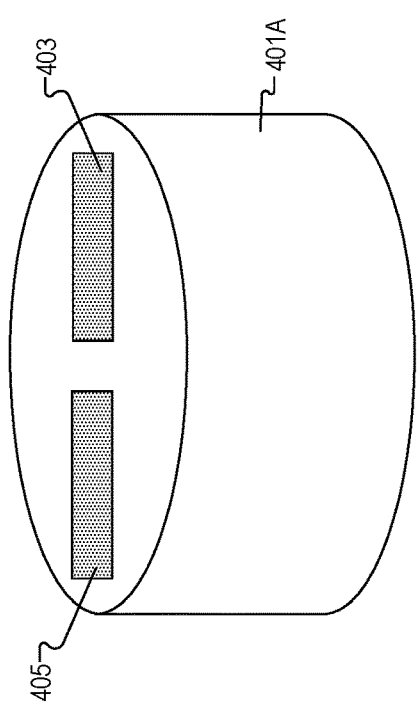

FIG. 4A depicts first rectangular shaped ultrasonic transducer 403 and second rectangular shaped ultrasonic transducer 405 disposed in plunger head 401A. As shown ultrasonic transducers 403/405 are disposed on opposite lateral sides of the plunger head 401A. In some embodiments, a piezo electric material may be directly exposed on the surface of plunger head 401A to form ultrasonic transducers 403/405. In other embodiments, ultrasonic transducers 403/405 may be coated with polymers or the like to protect the medication solution in the barrel of the device from contamination, and protect ultrasonic transducers 403/405 from corrosion or shorting. In one embodiment, first ultrasonic transducer 403 may be the transmitter and second ultrasonic transducer 405 may be the receiver, however, in other embodiments their roles may be reversed, and further still in other embodiments both ultrasonic transducer 403/405 send and receive the ultrasonic signals.

FIG. 4B depicts a series of first circular shaped ultrasonic transducers 403, and a series of second circular shaped ultrasonic transducers 405. As shown the transducers 403/405 are arranged in pairs, oriented in a triangular configuration on the surface of the plunger head 401B, and disposed proximate to the perimeter of the plunger head 401B. Unlike the embodiment depicted, in other embodiments, pairs of transducers may not be evenly spaced around the perimeter of plunger head 401B. Further, any number of pairs of transducers may be disposed around the perimeter of plunger head 401B including two pairs, four pairs, five pairs or the like. These sets of transducers may take the shape of a square, rectangle, pentagon, etc.

Figure 4C:
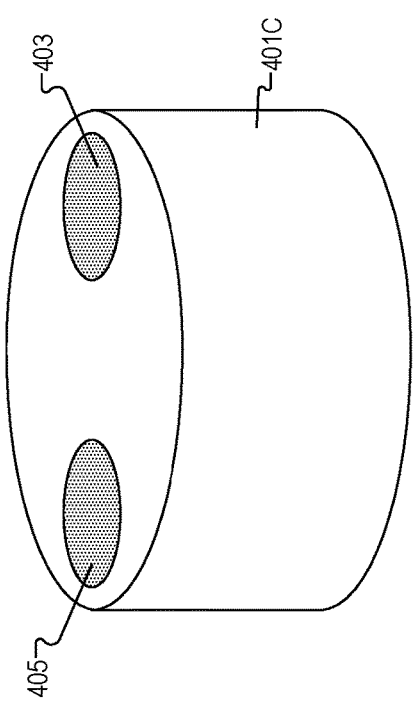

FIG. 4C depicts first circular shaped ultrasonic transducer 403 and second circular shaped ultrasonic transducer 405 disposed in plunger head 401C. As shown ultrasonic transducers 403/405 are disposed on opposite lateral sides of plunger head 401C. In some embodiments, ultrasonic transducers 403/405 may be oval shaped, egg shaped, amygdaloid, or the like.

FIG. 4D illustrates first semicircular shaped ultrasonic transducer 403 and second semicircular shaped ultrasonic transducer 405 disposed in plunger head 401D. As shown, ultrasonic transducers 403/405 are disposed on opposite lateral sides of plunger head 401D. In the illustrated embodiment, the outer edges of ultrasonic transducers 403/405 are concentric with the outer edge of plunger head 401D. However, in other embodiments the edges of ultrasonic transducers 403/405 may not be concentric with the outer edge of plunger head 401D.

Figure 4F:
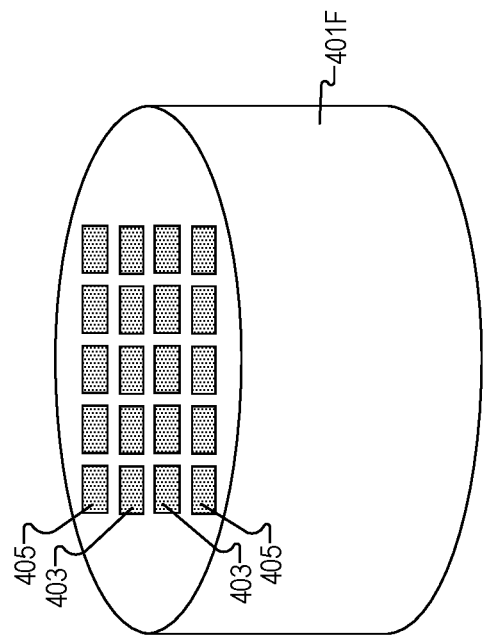
Figure 4E:
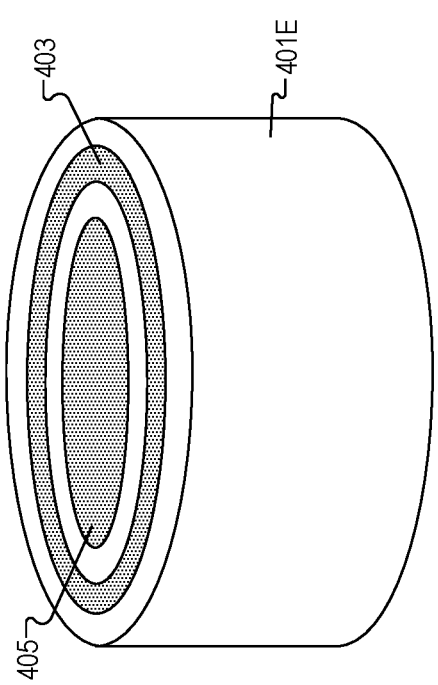

FIG. 4E depicts first circular shaped ultrasonic transducer 403 and second circular shaped ultrasonic transducer 405 disposed in plunger head 401E. As shown first circular shaped ultrasonic transducer 403 and second circular shaped ultrasonic transducer 405 are concentric. First ultrasonic transducer 403 is a ring (closed loop) and the second ultrasonic transducer 405 is positioned within the lateral bounds of the closed loop of first ultrasonic transducer 403. However, in other embodiments, the location of first and second ultrasonic transducers 403/405 may be reversed, or both ultrasonic transducers 403/405 may be rings. Additionally, the loop(s) may not be closed (open).

FIG. 4F illustrates a plurality of first rectangular shaped ultrasonic transducers 403 and a plurality of second rectangular shaped ultrasonic transducers 405 disposed in plunger head 401F. As shown ultrasonic transducers 403/405 are arranged into a 4×4 array; however, the organization can take other shapes such as a circular array, a ring of ultrasonic transducers 403/405 or the like. One of ordinary skill in the art will appreciate there are many ways to organize the plurality of ultrasonic transducers 403/405 into an array, in accordance with the teachings of the present disclosure.

Figure 5:
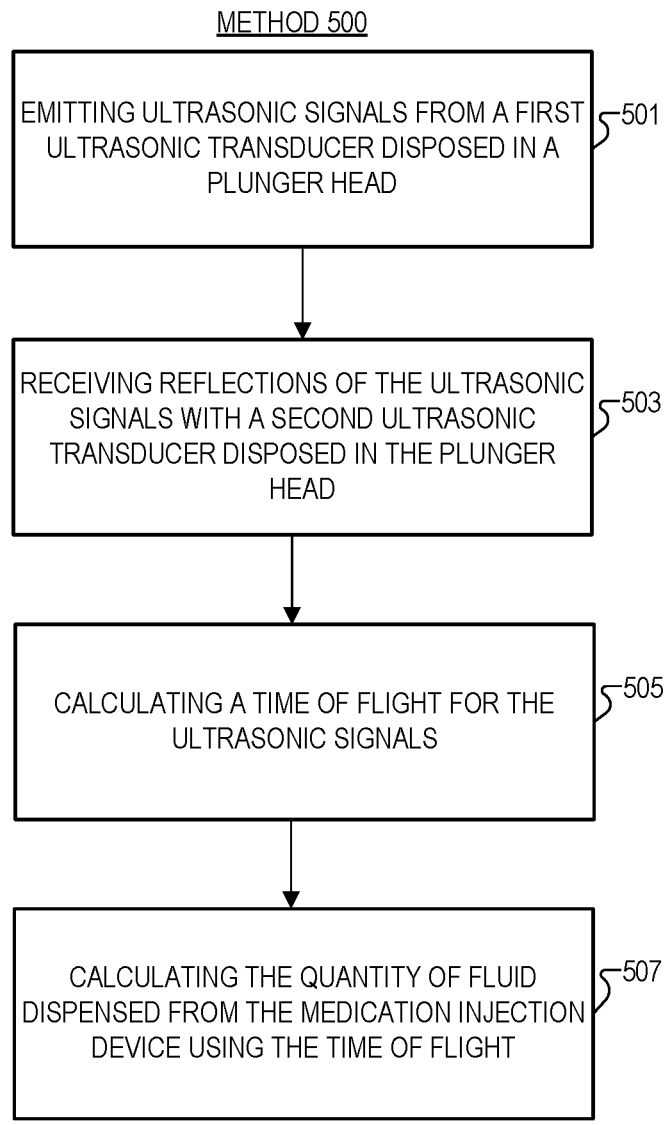
FIG. 5 illustrates a method of multi-transducer ultrasonic range finding, in accordance with an embodiment of the disclosure

FIG. 5 illustrates a method 500 of multi-transducer ultrasonic range finding, in accordance with an embodiment of the disclosure. The order in which some or all of process blocks 501-507 appear in method 500 should not be deemed limiting. Rather, one of ordinary skill in the art having the benefit of the present disclosure will understand that some of method 500 may be executed in a variety of orders not illustrated, or even in parallel. Further, blocks may be added to, or removed from, method 500 in accordance with the teaching of the present disclosure.

Block 501 shows emitting ultrasonic signals from a first ultrasonic transducer disposed in a first lateral side of the plunger head. As shown in FIG. 3, for example, ultrasonic signals travel from the first ultrasonic transducer along a length of a barrel of the medication injection device towards a dispensing end of the device. Once the signals reach a dispensing end of the barrel, a first side of a shoulder region of the barrel reflects the ultrasonic signals towards a second side of the shoulder region (opposite the first side). The second side of the shoulder region reflects the ultrasonic signals towards the second ultrasonic transducer. In the embodiment depicted in FIG. 3, the ultrasonic signals travel orthogonal to the length of the barrel between the first side of the shoulder region and the second side of the shoulder region.

Block 503 illustrates receiving reflections of the ultrasonic signals with a second ultrasonic transducer disposed in the second lateral side of the plunger head. In one embodiment, this may be measured as a change in voltage across a piezoelectric material in the plunger head.

Block 505 describes calculating, with a controller, a time of flight for the ultrasonic signals to travel from the first ultrasonic transducer to a dispensing end of the barrel and be reflected back into the second ultrasonic transducer. Time may be calculated with the microcontroller or with a dedicated timekeeping device coupled to the microcontroller.

Block 507 shows calculating the quantity of fluid dispensed from the medication injection device using the time of flight. In some embodiments this may be achieved by calculating a first position of the plunger head in the barrel using the time of flight, and calculating a second position of the plunger head in the barrel using the time of flight. The first and second positions may then be used to calculate a distance traveled by the plunger head using the first position and the second position. The distance then may be used to calculate the quantity of fluid.

Although depicted elsewhere, in some embodiments (e.g., FIG. 1), the medication injection device may transmit data indicative of the quantity of the fluid dispensed to an external device with a transmitter disposed in the medication injection device. The external device may graph and track the injections. The external device may plot the quantity of fluid dispensed for an extended period of time to show the user their medication injection history.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A plunger head for a medication injection device, comprising:
   a first ultrasonic transducer configured to emit ultrasonic signals, wherein the first ultrasonic transducer is oriented within the plunger head to send the ultrasonic signals along a length of a barrel of the medication injection device when the plunger head is disposed in the barrel;
   a second ultrasonic transducer, separate from the first ultrasonic transducer, disposed within the plunger head and oriented to receive reflections of the ultrasonic signals from a shoulder region of the barrel; and
   a controller disposed in the plunger head and coupled to the first ultrasonic transducer and the second ultrasonic transducer, wherein the controller includes logic that when executed by the controller causes the controller to perform operations including:
   instructing the first ultrasonic transducer to emit the ultrasonic signals.

2. The plunger head of claim 1, wherein the first ultrasonic transducer and the second ultrasonic transducer have at least one of a circular shape, an oval shape, a semicircular shape, or a rectangular shape.

3. The plunger head of claim 1, wherein the first ultrasonic transducer and the second ultrasonic transducer are disposed proximate to opposite lateral sides of the plunger head, and wherein when the plunger head is disposed in the barrel, the first ultrasonic transducer is oriented to emit the ultrasonic signals along the length of the barrel on a first side of the barrel, wherein the first side of the shoulder region of the barrel is oriented to reflect the ultrasonic signals towards a second side of the shoulder region opposite the first side of the shoulder region, and wherein the second side of the shoulder region is oriented to reflect the ultrasonic signals towards the second ultrasonic transducer along the length of the barrel on the second side of the barrel, and wherein the shoulder region includes a narrowing region of the barrel proximate to a dispensing end of the barrel.

4. The plunger head of claim 1, wherein the second ultrasonic transducer includes a first loop, and wherein the first ultrasonic transducer is positioned within the first loop and the first loop is closed, or wherein the first ultrasonic transducer includes a second loop, and wherein the second ultrasonic transducer is positioned within the second loop and the second loop is closed.

5. The plunger head of claim 1, further comprising a plurality of ultrasonic transducers arranged into an array, including the first ultrasonic transducer and the second ultrasonic transducer.

6. The plunger head of claim 1, wherein the controller further includes logic that when executed by the controller causes the controller to perform operations including:
   receiving a signal from the second ultrasonic transducer, in response to the second ultrasonic transducer receiving the ultrasonic signals; and
   calculating a time of flight for the ultrasonic signals to travel from the first ultrasonic transducer to a dispensing end of the barrel and be reflected back into the second ultrasonic transducer.

7. The plunger head of claim 6, wherein the controller further includes logic that when executed by the controller causes the controller to perform operations including:
   calculating a position of the plunger head based in part on the time of flight; and
   calculating a quantify of fluid dispensed from the barrel based in part on the position of the plunger head.

8. The plunger head of claim 1, wherein an emission bandwidth of the first ultrasonic transducer is greater than a receiving bandwidth of the second ultrasonic transducer, and wherein wavelengths in the emission bandwidth are included in the receiving bandwidth.

9. The plunger head of claim 1, wherein the controller further includes logic that when executed by the controller causes the controller to perform operations including:
  disabling the second ultrasonic transducer when the first ultrasonic transducer is emitting the ultrasonic signals.

10. A medication injection device, comprising:
  a barrel;
  a plunger disposed in the medication injection device;
  a plunger head disposed in the barrel and positioned to expel a fluid from the barrel when pushed by the plunger, wherein the plunger head includes:
  a first ultrasonic transducer disposed within the plunger head and oriented to send ultrasonic signals along a length of the barrel; and
  a second ultrasonic transducer, distinct from the first ultrasonic transducer, disposed within the plunger head and oriented to receive reflections of the ultrasonic signals from a shoulder region of the barrel; and
  a controller coupled to the first ultrasonic transducer and the second ultrasonic transducer, wherein the controller includes logic that when executed by the controller causes the controller to perform operations including:
  instructing the first ultrasonic transducer to emit the ultrasonic signals.

11. The medication injection device of claim 10, wherein the first ultrasonic transducer and the second ultrasonic transducer have at least one of a circular shape, an oval shape, a semicircular shape, or a rectangular shape.

12. The medication injection device of claim 10, wherein the second ultrasonic transducer includes a first loop, and wherein the first ultrasonic transducer is positioned within the first loop and the first loop is closed, or wherein the first ultrasonic transducer includes a second loop, and wherein the second ultrasonic transducer is positioned within the second loop and the second loop is closed.

13. The medication injection device of claim 10, further comprising a plurality of ultrasonic transducers arranged into an array, including the first ultrasonic transducer and the second ultrasonic transducer.

14. A plunger head for a medication injection device, comprising:
  a first ultrasonic transducer configured to emit ultrasonic signals, wherein the first ultrasonic transducer is oriented within the plunger head to send the ultrasonic signals along a length of a barrel of the medication injection device when the plunger head is disposed in the barrel;
  a second ultrasonic transducer disposed within the plunger head and oriented to receive reflections of the ultrasonic signals from a dispensing end of the barrel; and
  a controller disposed in the plunger head and coupled to the first ultrasonic transducer and the second ultrasonic transducer, wherein the controller includes logic that when executed by the controller causes the controller to perform operations including:
  instructing the first ultrasonic transducer to emit the ultrasonic signals;
  receiving a signal from the second ultrasonic transducer, in response to the second ultrasonic transducer receiving one of the reflections of the ultrasonic signals; and
  calculating a time of flight for one of the ultrasonic signals to travel from the first ultrasonic transducer to the dispensing end of the barrel and be reflected back to the second ultrasonic transducer.

15. A plunger head for a medication injection device, comprising:
  a first ultrasonic transducer configured to emit ultrasonic signals, wherein the first ultrasonic transducer is oriented within the plunger head to send the ultrasonic signals along a length of a barrel of the medication injection device when the plunger head is disposed in the barrel;
  a second ultrasonic transducer disposed within the plunger head and oriented to receive reflections of the ultrasonic signals from a shoulder region of the barrel; and
  a controller disposed in the plunger head and coupled to the first ultrasonic transducer and the second ultrasonic transducer, wherein the controller includes logic that when executed by the controller causes the controller to perform operations including:
  instructing the first ultrasonic transducer to emit the ultrasonic signals; and
  disabling the second ultrasonic transducer when the first ultrasonic transducer is emitting the ultrasonic signals.

* * * * *